Figure 1:
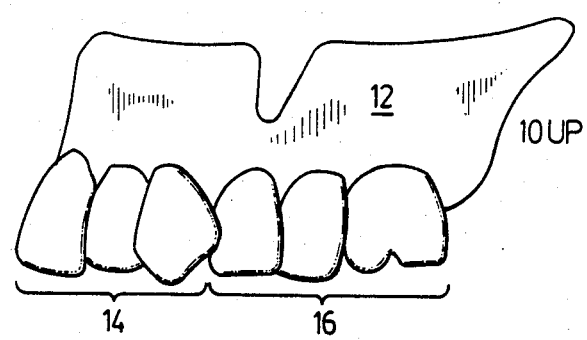

United States Patent [19]

Morris

[11] Patent Number: 4,657,509

[45] Date of Patent: Apr. 14, 1987

[54] DISPOSABLE IMPRESSION TRAY AND METHOD OF USING

[75] Inventor: Peter Morris, Mississauga, Canada

[73] Assignee: Kenneth A. Morrissey, Toronto, Canada

[21] Appl. No.: 765,818

[22] Filed: Aug. 15, 1985

[30] Foreign Application Priority Data

Feb. 22, 1985 [CA] Canada .................................. 474995

[51] Int. Cl.$^4$ .............................................. A61C 9/00
[52] U.S. Cl. ........................................ 433/37; 433/41; 433/171
[58] Field of Search .................... 433/171, 167, 37, 41

[56] References Cited

U.S. PATENT DOCUMENTS

| | | | |
|---|---|---|---|
| 3,644,996 | 2/1972 | Weinkle | 433/171 |
| 4,097,992 | 7/1978 | Hazar | 433/171 |
| 4,184,253 | 1/1980 | Tureaud | 433/171 |
| 4,227,877 | 10/1980 | Tureaud et al. | 433/37 |
| 4,247,287 | 1/1981 | Gigante | 433/171 |
| 4,259,074 | 3/1981 | Link | 433/37 |

FOREIGN PATENT DOCUMENTS 7901094  6/1980  PCT Int'l Appl. .................. 433/37

Primary Examiner—John J. Wilson

[57] ABSTRACT

A denture is made by providing an impression tray made of material malleable at less than 150° F. and rigid at body temperature, heating said tray and inserting it in the mouth while malleable and at less than 150° F., conforming it to the patient's mouth, measuring the vertical dimension of the patient's mouth, removing the tray, lining it with impression material, reinserting the tray to form a final impression, removing the tray, providing a bite block, attaching such blocks to the tray, inserting the tray in the patient's mouth, recording the bite registration, and using the resultant tray and bite blocks as the basis for forming a customized denture.

A disposable dental impression tray is made of material which may be rendered malleable at temperatures of less than 150° F., is substantially rigid at body temperature, has anterior teeth and is arranged to simulate a denture.

15 Claims, 11 Drawing Figures

DISPOSABLE IMPRESSION TRAY AND METHOD OF USING

This invention relates to a novel disposable dental tray for use in a process of making customized dentures, and to such process.

The disposable dental tray, in accord with the invention, is made of thermally softenable and preferably thermoplastic material and is fitted with simulated teeth (at least at the anterior locations) and generally formed to simulate a denture when placed in the patient's mouth. (The tray in accord with the invention may be embodied as a upper tray or as a lower tray.) The tray is provided with a channel from one side to the other on the side facing the patient's gums. In such channels, as described hereafter, impression materials may be placed to obtain the ridge impressions of the patient's mouth. In the case of an upper tray a web is provided to contact the vault of the mouth and impression material is placed in the web also.

It is preferred to provide upper dental trays, in accord with the invention which have both anterior and posterior teeth and upper and lower trays which have anterior teeth only. The trays, with anterior teeth only, are provided with attachment means, on their outer surface for mounting blocks of bite material thereon to obtain measurements defining the relative location of the patient's mandible and maxilla when his jaws are at the position defining the vertical dimension.

The trays in accord with the invention are made of material which is stable at body temperature but formable at temperatures below 150° F. The temperature criterion is because the patient can tolerate temperatures of under 150° F. in his mouth. However, temperatures of under 140° F. are generally more tolerable to the patient than those above that value. Any thermally formable material may be used. However, it is preferred to use a thermaplastic material in case the forming in accord with the invention has to be done more than once. We prefer to use methylmethacrylate.

The bite blocks used with the invention are made of material which is stable at body temperatures and malleable at temperatures below 150° F.

The method in accord with the invention includes the steps of:

(a) softening the dental tray or trays, (b) inserting the softened tray or trays in the patient's mouth at temperatures of under 150° F. and manually conforming it approximately to the ridges (i.e. gum area) therein and in the case of an upper tray to the vault, (c) either with or without the tray or trays in the patient's mouth determining a measure of the vertical dimension. The vertical dimension as the term is used herein is a measurement, unique to each patient, which relates to the relative position of the patient's upper and lower jaws with the mouth and lips closed. (It should be here explained that the true vertical dimension is not measured in the processes of this invention. What is measured is the vertical distance between the patient's nose and chin with the mouth and lips closed which is related to the true vertical dimension and is referred to herein as the 'vertical dimension measure',)

(d) with the formed tray or trays withdrawn from the patient's mouth the tray channels and the web if an upper tray is used are lined with impression material and the tray or trays replaced in the patient's mouth.

The patient then closes his mouth to the established vertical dimension measure, (e) the tray or trays is (are) again withdrawn from the mouth and bite blocks, rendered malleable, are attached to the means on the outer sides, (f) the tray or trays is reinserted in the mouth and the bite registration is recorded by having the patient close to the pre-recorded vertical dimension measure.

At this time the dentist may record the particulars of the final denture desired by the patient using the tray with its teeth as a datum. Thus the dentist will record the differences in tooth length between those required by the patient in his customized denture and those of the tray. The dentist will also record any differences in the desired tooth location from those on the tray. (For example the patient may desire the centre line to be to the right or left of that on the tray teeth or that the teeth have a larger or smaller gap or a different orientation than on the tray teeth). The dentist will record differences between the denture desired by the patient and the dental tray in colour, material, mould, rotation and shape of teeth and in the material and appearance of the denture base.

Subsequent to these operations a customized denture is constructed (usually in a dental laboratory remote from the dentist's office). This customized denture is constructed with the disposable dental tray, produced in the dentist's office, used as a datum, the customized denture embodying the patient's preferences as discussed above. The customized denture may be produced by conventional method well known to those skilled in the art and referred to briefly hereafter. However, two points should be noted. Firstly, the denture produced is truly customized just as dentures have been in the past. The disposable impression tray is discarded after the construction of the denture and its materials colour, teeth, do not (except in the sense that they act as reference datums) affect the characteristics of the customized denture. Secondly, the customized denture has been made with many less visits to the dentist's office than with prior methods.

As stated, with the disposable tray prepared as outlined above and the measurements described, a customized denture may be prepared in a dental laboratory by a series of steps, using conventional techniques.

The more important of these steps using conventional techniques are:

Stone models (or equivalent models) are formed of the final impressions in the impression trays. Each stone model and the corresponding impression tray is mounted on an articulator and adjusted to duplicate the functions of the patient's maxilla and mandible. The models are marked to provide indications of the vertical dimension and the desired mid or centre line of the anterior teeth. (The vertical dimension indication marked on the stone model is not obtained from the vertical dimension measure but from the impressions in the bite blocks). The trays are removed, bearing the final impressions, from the stone model, to expose the molded area of the stone model. A wax model is formed of the required denture on the moulded area and a denture is thereafter formed from the wax model in the conventional manner.

The inventive disposable denture tray and the related method of making dentures has a number of advantages over the prior art. Relative to the conventional method of making customized dentures the inventive means and method provide customized dentures of equal quality which employ conventional techniques in the dental laboratory but requiring many less visits to the dentist's office. The inventive method allows the taking of ridge impressions, production of bite block impressions, recording of desired teeth size, colour, spacing and orientation to be performed in one visit to the dentist's office instead of on separate visits.

In distinction to conventional prior art method of making customized dentures there are also prior methods of making finished dentures using thermoplastic material having real teeth therein. These are not customized dentures but would be prefabricated to be applied to a range of patients. Thus the patient with such a prefabricated denture has no choice or very limited choice as to colour, tooth size etc. Moreover, the denture being thermoplastic is susceptible to deformation if the user encounters food or liquid temperatures above the creep or softening temperatures of the thermoplastic. Since such prefabricated denture are solely prepared in the dentist's office the benefit of laboratory expertise and equipment is not available. Thus, such dentures are of value for a temporary purpose only until suitable customized dentures can be prepared.

Other features and advantages of the invention will be discussed in the description of the specific embodiment to follow.

In drawings which illustrate a preferred embodiment of the invention.

Figure 2:
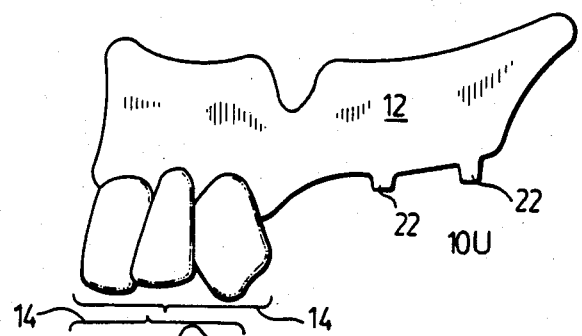
Figure 3:
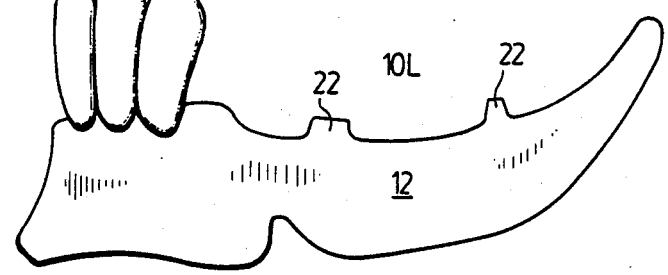
Figure 4:
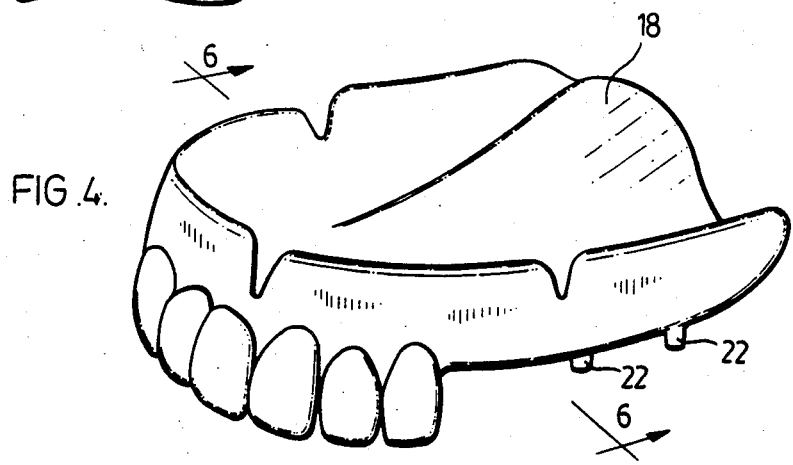
Figure 5:
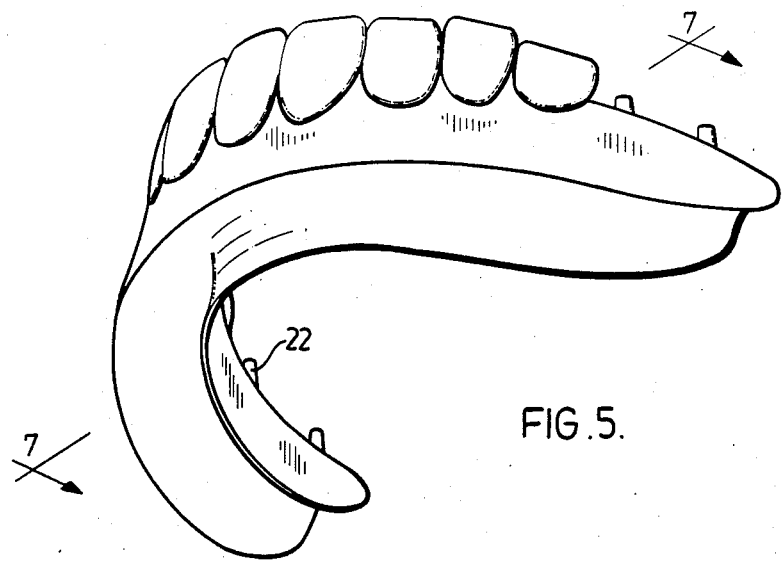
Figure 6:
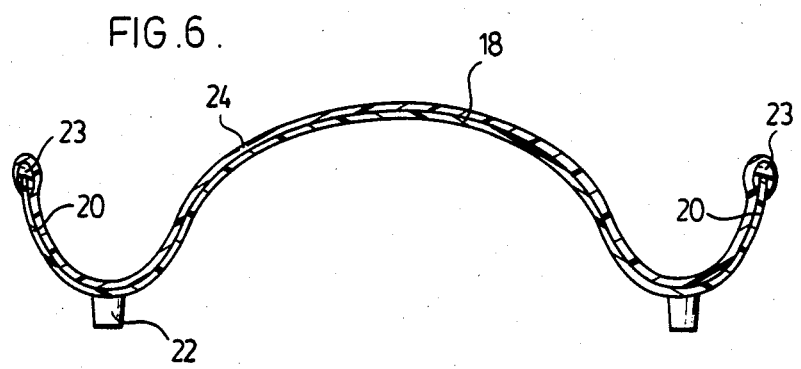
Figure 7:
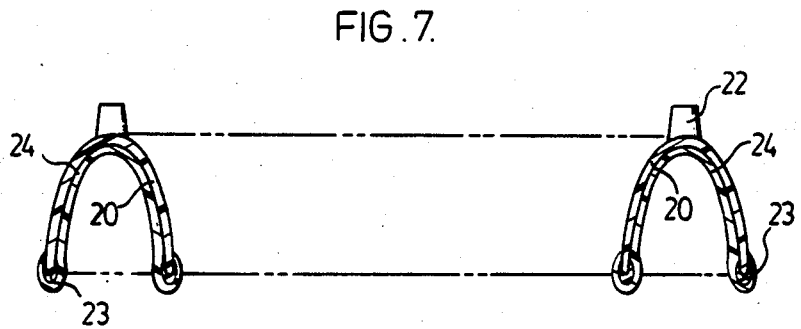
Figure 8:
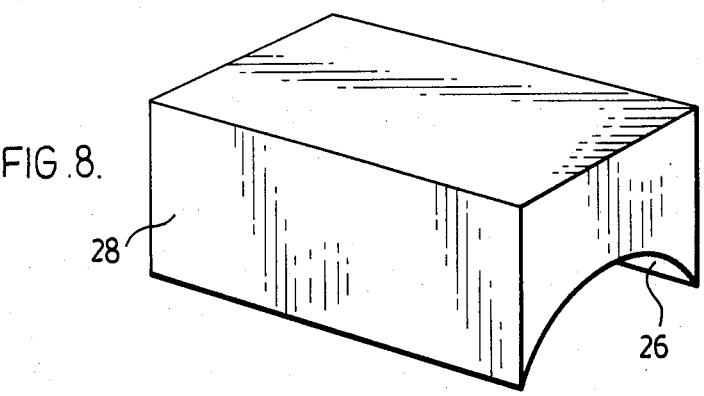
Figure 9:
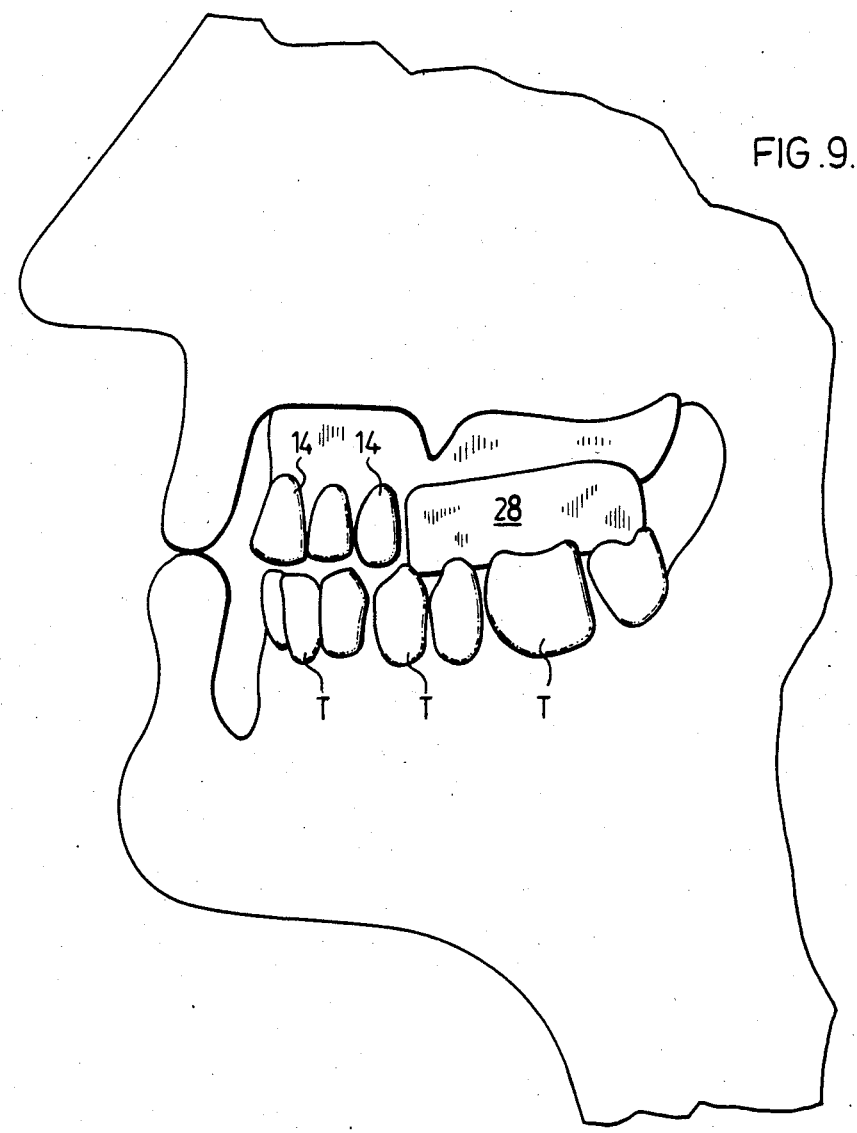
Figure 10:
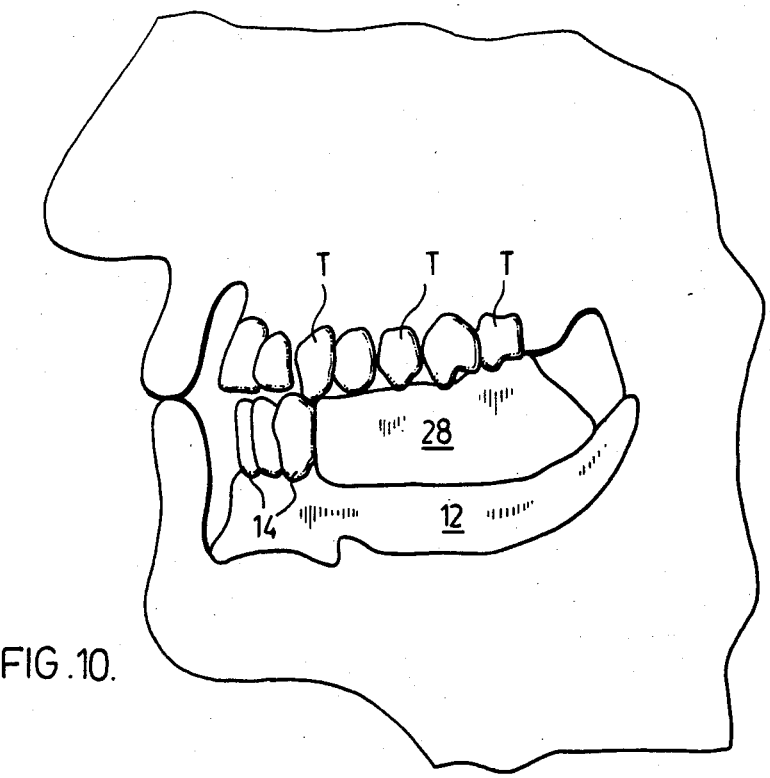
Figure 11:
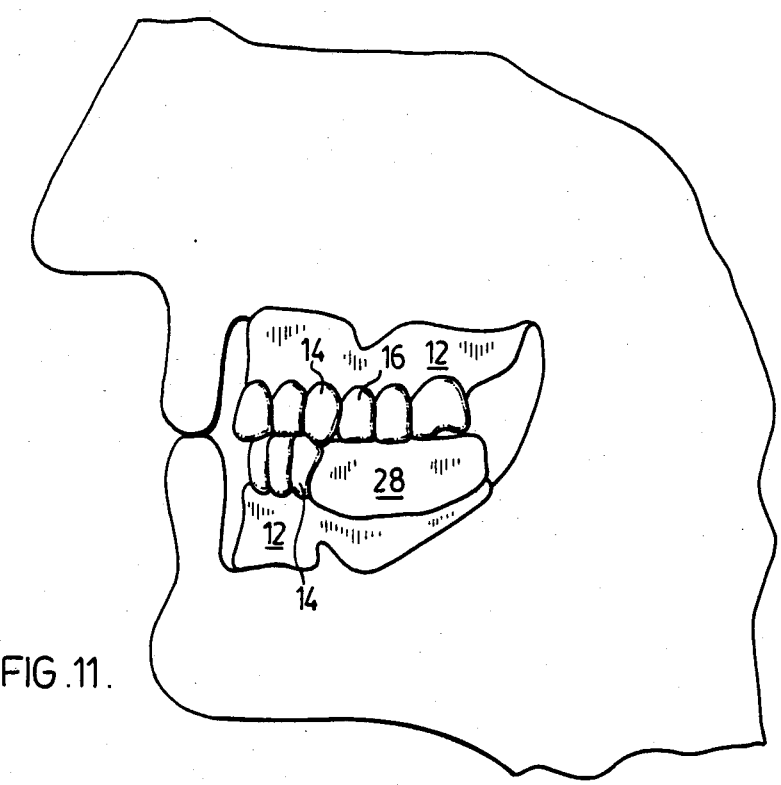

FIG. 1 is a side view of an upper disposable impression tray with posterior teeth, FIG. 2 is a side view of an upper disposable impression tray without posterior teeth, FIG. 3 is a side view of a lower disposable impression tray, FIG. 4 is a perspective of the tray of FIG. 2, FIG. 5 is a perspective view of the tray of FIG. 3, FIG. 6 is a cross-section along the line 6—6 of FIG. 4, but having impression material and muscle mold material added, FIG. 7 is a cross-section along the line 7—7 of FIG. 5, but having impression material and muscle mold material added, FIG. 8 is a perspective view of a bite block, FIG. 9 shows the upper tray with bite block in place to form an upper denture, FIG. 10 shows a lower tray with bite block in place to form a lower denture, FIG. 11 shows both upper and lower trays in place to form both upper and lower dentures.

In the drawings 10U, 10UP, 10L illustrate disposable dental impression trays in accord with the invention. Their most notable feature is that they generally visually and physically (to the extent discussed herein) simulate dentures to assist dentist and patient in judging appearance. Tray 10U shows an upper tray without posterior teeth, tray 10UP shows an upper tray with posterior teeth and tray 10L shows a lower tray shown without posterior teeth as will usually be the case. It will be noted that upper trays 10U, and 10UP will be provided with central webs 18 to fit (approximately) against the roof of the mouth. It will also be noted that trays 10U and 10L having anterior teeth only have studs 22 where the posterior teeth would be for the attachment of bite blocks. The body 12 of each tray is formed of material deformable at temperatures of under 150° F. but stable at room temperatures. It will be preferable if the material is thermoplastic in case the deformation has to be done two or more times. We prefer to use methylmethacrylate as the material. The body 12 is provided with anterior teeth 14 and the body of tray 10UP is also provided with posterior teeth 16. The teeth are preferably made of the same material as the body or, if desired, may be of different material. In either case, it will be remembered that the teeth 14 or 16 have no direct relationship in material, colour size etc. to the teeth which will appear in the customized final denture. The body 12 may if desired be made of transparent material. This will assist in detecting whitened pressure spots on the gums if the tray body before or after deformation is exerting undue pressure on the gums or vault. The teeth will be coloured and shaped to simulate real teeth since this will assist patient and dentist in visualizing the desired appearance of the final denture when looking at the tray. The arms of trays 10UP, 10P and 10L are shaped to form U shaped channels 20 oriented to face the gum ridges of the maxilla (tray 10UP or 10U) or mandible (tray 10L). The channels are large enough to receive such ridges when containing a lining of impression material. The upper body 10P or 10UP is also provided with a central web 18 shaped generally to conform to the vault of the maxilla.

It will be customary for the dentist to carry a small range of sizes of such disposable trays to fit patient's jaws of various sizes and shapes. The tray is used as follows:

Step 1. Uses with a patient requiring both upper and lower plates, suitable trays 10 UP and 10L will be selected. The selection of a plate 10UP is usually made after measuring the distance between the tuberosities of the mouth (or of the old denture if available). In the case of the tray 10L the selection is usually made after measurement of the retromolar pad area.

Step 2. The upper tray is formed after immersing it in a hot water bath (165°–175° F.) until it becomes malleable (which usually requires about 30 seconds). The tray 10UP is (after cooling to less than 150°) then inserted in the patients mouth and by exerting light alternative digital pressure over the area of the body including web 18 and channels 20, is conformed generally to the shape of the ridge and vault of the maxilla.

Step 3. The selected tray is border or muscle moulded by adding to the periphery of the arms a conventional material 23 for this purpose, such as wax, silicon or another composition and with this supplementary material the borders of the tray are shaped to coincide with all of the anatomical landmarks of the oral cavity and to extend the tray periphery so as not to interfere with any of the muscular attachments. The material selected must be malleable in use and later set to a rigid shape. Some materials used, such as wax, will naturally adhere to the tray body. Other material such as silicone will require adhesive.

Step 4. Steps 2 and 3 are then repeated for the lower tray, it being noted, that without a central web the lower tray is deformed to fit the mandible ridge only.

Step 5. With the trays 10UP and 10L removed from mouth, at the dentist's preference, the vertical dimension measure (which determines the relative position of the maxilla and mandible with the mouth just closed) is obtained by measuring the distance with the mandible and lips in the normal closed position. The upper and lower trays are replaced in the mouth and, if necessary, remove any interference between tray teeth or body so that patient may close until the pre-established vertical dimension is established.

Step 6. Remove the trays from the mouth and line their channels and the web of tray 10 UP with final impression material 24 (see FIG. 6 and 7). Reinsert the lined trays in mouth and press each tray against its corresponding ridge (and the upper against the vault) to form the final impression of the dental base area at jaw closure as determined by the vertical dimension measure. The final impression material will be of a type to remain mouldable for a short period and then set to rigid form. Many varieties are well known to those skilled in the art and include plaster of paris and other materials sold under private brand names.

Step 7. Remove the trays from the mouth and attach bite blocks 28 to the studs 22 of tray 10L. The bite blocks 28 are preferably rectilinear blocks as shown in FIG. 8 with a concave side 26 directed to extend longitudinally in position to be attached to the outer studs 30 on trays 10U or 10L (here 10L). The bite blocks 28 are of thermoplastic material designed to be malleable at less than 150° C. and rigid at room temperature. In the example being discussed, bite blocks 28 for each arm of tray 10L are softened in hot water and applied to the studs 22 of the tray. The upper and lower trays 10UP and 10L are then reinserted in the mouth and the bite registration is recorded in the bite material by having the patient close into the softened bite rim to the preestablished vertical dimension measure. The vertical dimension is then remeasured with the calipers and recorded in the directions to the dental laboratory. The position achieved in this step is shown in FIG. 11.

Step 8. The dentist will then mark any changes in tooth length and mid line (i.e. the line between the two front teeth) both on the directions to the dental lab and on the relevant tray which, in the dental lab, will act as a datum in the making of the final denture. The anteroposterior position of the anterior teeth is checked and the patient's selections as to material shape, rotation and shade or colour of teeth and the material of the desired denture base are recorded.

(Steps 9 and 10 are customarily performed in the dental laboratory. Each step is only referred to briefly as it is performed in accord with well known techniques).

Step 9. In the dental laboratory, stone models are formed of the final impressions in the selected trays. The stone models and trays are mounted in an articulator and adjusted to duplicate the functions of the patients maxilla and mandible. The stone models are marked to provide an indication of the required vertical dimension and the center line of the anterior teeth. (It will be noted that the trays have now served their entire function and may be discarded).

Step 10. The trays are removed, from the stone models to expose the latters' moulded area. A wax model is formed of the required denture on the moulded area and a denture is then formed from the wax model in the conventional manner.

If in the process described above, an upper tray 10U without posteriors was used then bite blocks would be applied to both trays in Step 7.

If the patient only request an lower plate then lower tray 10L only will be used and the bite blocks 22 attached thereto in Step 7. The invention using tray 10L only to get the bite block impression is shown in FIG. 10. It will be noted that the lower tray 10L and its bite blocks cooperate with the patient's natural upper teeth T. In the dental laboratory the lower tray is used with a conventional upper impression tray device on the articulator.

If the patient only requires an upper plate, then upper tray 10U only will be used and only the steps relevant thereto will be carried out in the dentist's office. The invention using tray 10U only to get the bite block impression is shown in FIG. 9. It will be noted that the upper tray 10U and its bite blocks cooperate with the patient's natural lower teeth T. In the dental laboratory the upper tray is used with a conventional lower impression tray device in the articulator.

I claim:

1. Method of making a denture, comprising:
   providing at least one of an upper and lower impression tray made of material which is malleable at temperatures of less than 150° F. and which is substantially rigid at body temperature, which tray has front teeth arranged with said tray to simulate a denture,
   heating said at least one tray to a temperature at which it is malleable,
   inserting said heated tray at a temperature of less than 150° F. but still in malleable condition into the patient's mouth and conforming at approximately to the ridge of the patient's jaw,
   at some time prior to the forming of the final impression, measuring the vertical dimension measure of the said upper and lower jaws,
   removing such at least one tray from the patient's mouth,
   lining said at least one tray with impression material,
   reinserting the tray in the patient's mouth to form final impression of the dental base area with the jaws at said vertical dimension measure,
   providing a bite block of material which is malleable at temperatures under 150° F. and rigid at room temperature,
   rendering such bite blocks malleable and attaching such bite rims to said at least one tray and inserting the tray with the bite block so attached into the patient's mouth and recording the bite registration with the jaws held to the attitude required by said vertical dimension measure,
   using the resultant tray and bite blocks as the basis for forming a customized denture.

2. The method as claimed in claim 1 wherein the forming of customized dentures includes the steps of:
   forming models of the final impression,
   mounting models and trays in an articulator and adjusting such articulator to duplicate the functions of the patient's maxilla and mandible,
   removing the tray bearing the final impression from the stone model to expose the moulded area of the stone model,
   forming a wax model of the required denture on the moulded area,
   forming a denture from the wax model in a conventional manner.

3. Method as claimed in claim 2 including the steps of determining relative to said at least one impression tray, the tooth length and mid line desired in the customized denture,
   marking the model of the final impression to provide an indication of the required vertical dimension measure and of the midline desired.

4. Method as claimed in claim 1 including the steps of determining relative to said at least one impression tray, the tooth length and midline desired in the customized denture.

5. Method of making a customized denture, comprising:

providing at least one of an upper and lower impression tray made of material which is malleable at temperature of less than 150° F. and which is substantially rigid at body temperatures, which tray has front teeth arranged with such tray to simulate a denture, heating said at least one tray to a temperature at which it is malleable, inserting said heated tray at a temperature of less than 150° F. but still in malleable condition into the patient's mouth and conforming at approximately to the ridge of the patient's jaw, removing such at least one tray from the patient's mouth, measuring the vertical dimension measure of said upper and lower jaws prior to lining the trays with impression material, lining the trays with impression material, reinserting the tray in the patient's mouth to form final impression of the dental base area with the jaws conforming to said vertical dimension measure, providing bite block material which is malleable at temperatures under 150° F. and rigid at room temperatures, rendering bite blocks malleable, attaching to each tray in location to measure bite and insert at a temperature of less than 150° F. in patient's mouth and recording bite registration with the maxilla and mandible conforming to vertical dimension measure, using such lined tray, bite impressions and recorded measurements as a basis for making conventional customized denture.

6. Disposable dental impression tray made of material which may be rendered malleable at temperatues of less than 150° F. and which is substantially rigid at body temperature, which tray has anterior teeth and is arranged to simulate a denture, said tray being without posterior teeth and having on each side at posterior teeth locations means for attachment of bite material.

7. Disposable dental impression tray as claimed in claim 6 wherein said bite material is thermoplastic.

8. Disposable dental impression tray as claimed in claim 7 wherein said tray material is thermoplastic.

9. Disposable dental impression tray as claimed in claim 6 wherein said tray material is thermoplastic.

10. Disposable dental impression tray as claimed in claims 7 or 9 wherein said anterior teeth are made of thermoplastic material.

11. Disposable dental impression tray as claimed in claims 7 or 9 wherein said tray is made of transparent material.

12. Disposable dental impression tray made of material which may be rendered malleable at temperatures of less than 150° F. and which is substantially rigid at body temperature, which tray has anterior teeth and is arranged to simulate a denture, said tray being without posterior teeth and having on each side at posterior teeth locations attached bite material of a type which is malleable at temperatures of under 150° F. and rigid at body temperature.

13. Disposable dental impression tray as claimed in claim 12 wherein said tray material is thermoplastic.

14. Disposable dental impression tray as claimed in claims 6 or 7 wherein said anterior teeth are made of thermoplastic material.

15. Disposable dental impression tray as claimed in claims 6 or 12 wherein said tray is made of transparent material.

* * * * *